United States Patent
Yamashita

(10) Patent No.: US 7,032,208 B2
(45) Date of Patent: Apr. 18, 2006

(54) DEFECT INSPECTION APPARATUS

(75) Inventor: Kyoji Yamashita, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 321 days.

(21) Appl. No.: 10/395,342

(22) Filed: Mar. 25, 2003

(65) Prior Publication Data

US 2003/0197857 A1 Oct. 23, 2003

(30) Foreign Application Priority Data

Mar. 27, 2002 (JP) ........................... 2002-089957

(51) Int. Cl.
G06F 17/50 (2006.01)
G01N 21/00 (2006.01)
G01N 21/84 (2006.01)
G06K 9/00 (2006.01)

(52) U.S. Cl. ............... 716/19; 356/237.2; 356/430; 382/149

(58) Field of Classification Search ........ 716/19, 716/20, 21; 356/237–430; 382/144–149; 250/491.1

See application file for complete search history.

(56) References Cited

U.S. PATENT DOCUMENTS

| 4,559,603 | A | | 12/1985 | Yoshikawa | |
| 5,185,812 | A | * | 2/1993 | Yamashita et al. | 382/145 |
| 5,404,410 | A | * | 4/1995 | Tojo et al. | 382/144 |
| 5,772,603 | A | * | 6/1998 | Ohlsson et al. | 600/509 |
| 5,960,106 | A | * | 9/1999 | Tsuchiya et al. | 382/144 |
| 6,084,716 | A | * | 7/2000 | Sanada et al. | 359/629 |
| 6,396,943 | B1 | * | 5/2002 | Yamashita | 382/144 |
| 6,473,525 | B1 | * | 10/2002 | Cheung et al. | 382/199 |
| 6,674,890 | B1 | * | 1/2004 | Maeda et al. | 382/149 |
| 2001/0055416 | A1 | * | 12/2001 | Yamashita | 382/149 |
| 2002/0054293 | A1 | * | 5/2002 | Pang et al. | 356/430 |
| 2003/0095251 | A1 | * | 5/2003 | Maeda et al. | 356/237.2 |
| 2004/0075837 | A1 | * | 4/2004 | Maeda et al. | 356/394 |
| 2004/0086170 | A1 | * | 5/2004 | Shishido et al. | 382/149 |

FOREIGN PATENT DOCUMENTS

JP 5-281155 10/1993

* cited by examiner

Primary Examiner—Leigh M. Garbowski
Assistant Examiner—Magid Y. Dimyan
(74) Attorney, Agent, or Firm—Oblon, Spivak, McClelland, Maier & Neustadt, P.C.

(57) ABSTRACT

A defect inspection apparatus includes a sensor which optically senses a circuit pattern formed on a plate to be inspected to obtain scanned image data thereof while moving relatively to the plate, an AD converter which converts the scanned image data into digital form, a normal image data generator which generates normal image data expressed by use of multiple values based on CAD data relating to the circuit pattern, a reference data generator which filters the normal image data to generate reference data while selecting filter coefficients according to the moving direction of the plate to be inspected by use of a finite response filter having asymmetrical coefficients, and a comparator which compares the reference data with the scanned image data.

16 Claims, 10 Drawing Sheets

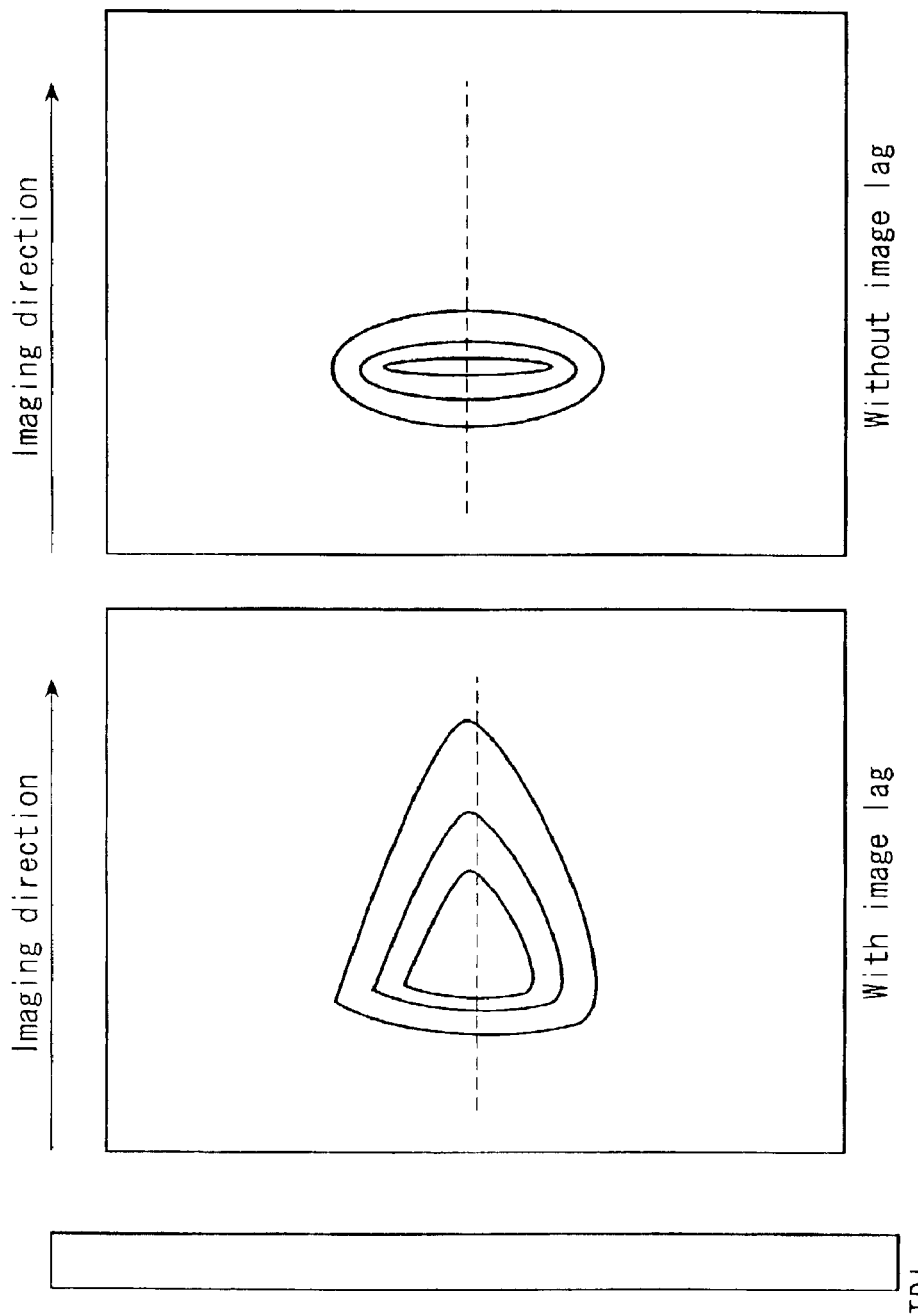
FIG. 10A With image lag
FIG. 10B Without image lag

DEFECT INSPECTION APPARATUS

CROSS-REFERENCE TO RELATED APPLICATIONS

This application is based upon and claims the benefit of priority from the prior Japanese Patent Application No. 2002-089957, filed Mar. 27, 2002, the entire contents of which are incorporated herein by reference.

BACKGROUND OF THE INVENTION

1. Field of the Invention

This invention relates to a defect inspection apparatus and more particularly to a defect inspection apparatus which is suitable for inspection of liquid crystal substrates, printed circuit boards and photomasks used for manufacturing semiconductor devices.

2. Description of the Related Art

Semiconductor devices have been manufactured by exposing a circuit pattern that is formed on a photomask onto a silicon wafer using photolithography techniques. In this case, if a unallowable defect such as a pinhole or a pindot may exist on a mask pattern, the defect will be printed onto every wafer and will decrease yield of semiconductor devices. Therefore, it is crucial to detect critical defects on a photomask and repair the defects before exposing a photomask onto a wafer.

In order to detect defects of a mask pattern that are formed on a photomask, not only a die-to-die inspection method but also a die-to-database inspection method have been adopted. A die-to-database inspection method compares scanned image data obtained by optically scanning mask patterns and comparing the image with reference data obtained based on CAD (computer-aided design) data, and a die-to-die inspection method compares adjoining patterns sharing the same CAD data with each other. A die-to-die inspection method is easy to implement, whereas there is a risk that common defects that are located in the same spot of the adjoining patterns may fail to be detected. Since scanned image data is compared with CAD data in the die-to-database inspection method, a die-to-database inspection technique is more reliable, whereas it is a difficult task to conform the reference data to the scanned image data. As a result, difference between the reference data and the scanned image data may cause a false alarm and thus it is a difficult task to implement die-to-database inspection with high sensitivity.

As semiconductor devices become more and more integrated, a critical defect on a mask becomes smaller and smaller. It is required to enhance defect sensitivity. In order to enhance sensing sensitivity, it is necessary to generate high-fidelity reference image data to conform it to the scanned image data. In particular, major factors that may reduce inspection sensitivity includes aberration of an objective lens and an image lag of a time and integration (TDI) CCD sensor. However, it takes plenty of cost and time to design and fabricate a diffraction-limited objective lens at a wavelength of ultraviolet rays or deep ultraviolet rays in order to enhance modulation transfer function (MTF). Also, it is difficult to obtain image quality in an image of high signal-to-noise ratio. In particular, an image lag in a TDI sensor is partly due to recombination of an electron and a hole at a deep ultra-violet wavelength.

Further, methods for generating reference data have been researched and developed in order to enhance the degree of fidelity to the scanned image data. For example, optimization of optimal digital filter coefficients or the like based on scanned data is considered. However, conventionally, since the conventional modeling process is not complete because the process does not distinguish each factor such as aberration and an image lag, sufficient results have not been obtained.

Thus, in the conventional defect inspection apparatus, it is crucial to use the die-to-database inspection method in order to make a more reliable inspection, but it is difficult to enhance the degree of fidelity of the reference data to the scanned image data, thereby to reduce the inspection sensitivity. Therefore, it is desired to implement a defect inspection apparatus which enhance the degree of conformity of the reference data to the scanned image data, prevent occurrences of false defects, and make defect inspection more reliable by accurately modeling the characteristic of the scanned image data to generate the reference data.

BRIEF SUMMARY OF THE INVENTION

A defect inspection apparatus according to a first aspect of the invention comprises:

a stage on which a plate to be inspected having a circuit pattern is mounted and which is movable in an X direction and in a Y direction that is perpendicular to the X direction;

a sensor which optically senses the circuit pattern to obtain scanned image data;

a scanned image data memory which stores the scanned image data in gray level;

a normal image data generator which generates normal image data expressed in gray level based on computer-aided design data relating to the circuit pattern;

a reference data generator which converts the normal image data to generate reference data, the reference data generator including a positional corrector which corrects the position data of the normal image data, a filtering part which subjects the normal image data to a filtering process, and a filter coefficient selector which has a plurality of sets of filter coefficients, selects one of the sets of filter coefficients and extracts the desired filter coefficients used in the filtering part from the one selected from the sets of filter coefficients; and a comparator which compares the reference data with the scanned image data.

A defect inspection apparatus according to a second aspect of the invention comprises:

a sensor which optically senses a circuit pattern formed on a plate to be inspected to obtain scanned image data of the circuit pattern while moving relatively to the plate to be inspected;

an analog-to-digital converter which converts the scanned image data into gray level;

a normal image data generator which derives normal image data expressed in gray level based on computer-aided design data relating to the circuit pattern;

a reference data generator which filters the normal image data to generate reference data while selecting filter coefficients according to a moving direction of the plate to be inspected by use of a finite response filter having asymmetrical coefficients; and a comparator which compares the reference data with the scanned image data.

A defect inspection method for a plate to be inspected having a circuit pattern formed thereon according to another aspect of the invention comprises:

optically scanning the circuit pattern while moving the plate to be inspected and a sensor relative to each other;

generating normal image data expressed in gray level based on computer-aided design data relating to the circuit pattern;

filtering the normal image data to generate reference data while switching filter coefficients according to a moving direction of the plate to be inspected by use of a finite response filter having asymmetrical coefficients; and comparing the reference data obtained from the reference data generator with the scanned image data obtained with the sensor.

BRIEF DESCRIPTION OF THE SEVERAL VIEWS OF THE DRAWING

FIGS. 10A and 10B are diagrams showing an image lag and the effect of a filtering process.

DETAILED DESCRIPTION OF THE INVENTION

In this invention, reference data having higher degree of conformity with respect to scanned image data can be generated by accurately modeling the scanned image data characteristic by switching filter coefficients according to the relative moving direction of a plate to be inspected and sensor by use of a reference data generator configured by a finite response filter having asymmetrical coefficients. As a result, it becomes possible to prevent occurrences of false defects and perform defect inspection with high sensitivity.

There will now be described an embodiment of the present invention with reference to the accompanying drawings.

Embodiment

Figure 1:
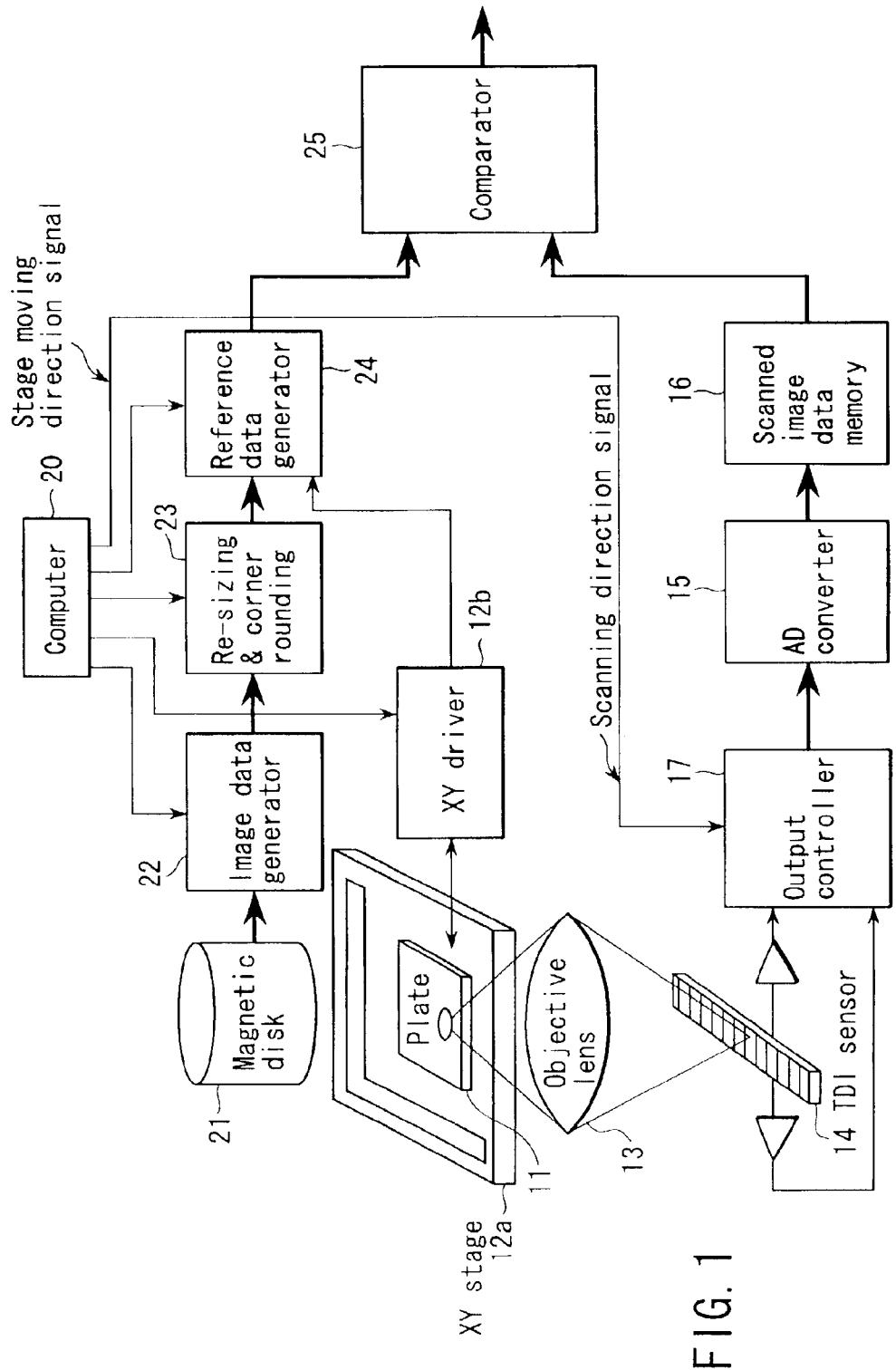
FIG. 1 is a schematic configuration diagram showing a defect inspection apparatus according to one embodiment of the present invention.

FIG. 1 is a schematic configuration diagram showing a defect inspection apparatus according to one embodiment of the present invention.

A plate to be inspected 11 such as a photomask is mounted on an XY stage 12a, and an XY driver 12b which drives the XY stage 12a is driven in an X and a Y directions on a horizontal plane by control of a computer 20. An optical image of the plate to be inspected 11 is formed on a CCD (TDI) sensor 14 by an objective lens 13 and thus scanned image data is obtained.

Figure 2:
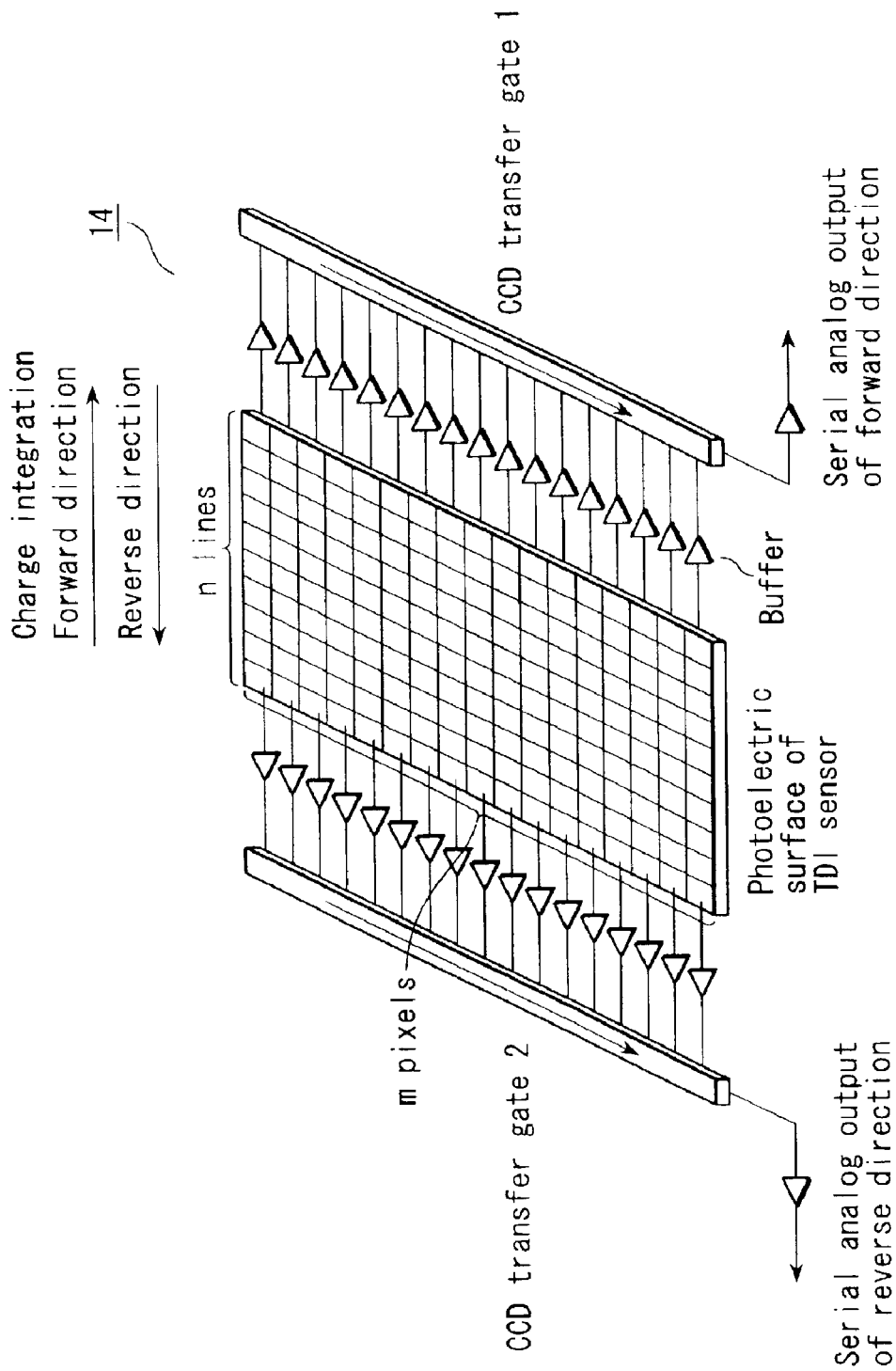
FIG. 2 is a schematic view showing the configuration of a TDI sensor used in the present embodiment.

The TDI (Time delay and Integration) sensor 14 is configured as shown in FIG. 2, for example, and has a photoelectric surface of m pixels×n lines. In the case where charges are integrated and transferred in a forward direction with respect to the line arrangement direction, the charges are discharged into a CCD transfer gate 1 via a buffer and output as a serial analog signal of a forward direction. On the other hand, in the case where charges are integrated and transferred in the backward direction with respect to the line arrangement direction, the charges are discharged into a CCD transfer gate 2 via a buffer and output as a serial analog signal of a backward direction.

More specifically, in the case of FIG. 1, scanned image data along the X direction can be obtained by sensing a pattern by use of the TDI sensor 14 while moving the XY stage 12a in the X direction, for example. The scanned data is input to an output controller 17. This is because outputs of the TDI sensor are provided on the right and left sides in FIG. 1 is that the charge integration direction can be set in either the forward direction or the backward direction.

The output controller 17 determines whether input from the TDI sensor 14 is a signal of a forward direction or a backward direction based on information of a scanning direction signal from the computer 20 and supplies a serial analog signal of a corresponding direction to an analog-to-digital converter 15. After the serial analog signal is digitized by the analog-to-digital converter 15, the digital data is temporarily stored in a scanned image data memory 16.

A normal image data generator 22 forms image data expressed in gray level based on CAD data stored on a magnetic disk 21. The image data is processed by a resizing-and-corner-rounding part 23 and then supplied to a reference data generator 24. The reference data generator 24 is supplied with positional coordinates of the XY stage 12a and reference data is formed based on image data of an area that corresponds to the positional coordinates.

The scanned image data temporarily stored in the scanned data memory 16 and the reference data formed in the reference data generator 24 are both supplied to a comparator 25. The comparator 25 compares the scanned image data and the reference data with each other and detects portions which do not conform with each other as a defect. That is, if the difference between the scanned image data and the reference image data is below the allowable threshold, the difference is neglected. On the other hand, if the difference between the data items exceeds the allowable threshold, the difference is considered as a defect.

The normal configuration explained so far is basically the same as that of the conventional apparatus, but in the present embodiment, a filtering process with high precision is performed in the reference data generator 24.

That is, the reference data generator 24 generates the reference data by performing a process for correcting the position based on the positional coordinates of the XY stage 12a and a filtering process for simulating the optical characteristic by using image data supplied from the image data generator 22. The above method is disclosed in detail in U.S. Pat. No. 4,559,603, "Apparatus for inspecting a circuit pattern drawn on a photomask used in manufacturing large scale integrated circuits", for example. In the disclosure, the measurement position and the position of the stage are derived by digitizing a signal which is obtained by scanning a mask pattern in a direction perpendicular to the stage moving direction and reference information is derived based on information of the sensitivity characteristic in a minute area on the pattern and a designed value. Then, the reference information and measured information are compared with each other to determine whether the pattern is abnormal or not.

In this case, if a Gaussian filter is used for the filtering process for simplicity, it is considered that an asymmetrical image lag due to the aberration of an objective lens 13 and the dynamic characteristic of a TDI sensor 14 occurs and the scanned image data and reference data do not conform with each other. There is a risk that the non-coincidence may cause a false defect, and therefore, it is necessary to create reference data as accurately as possible in accordance with the scanned image data in order to perform the defect inspection with high sensitivity. For this purpose, in the present embodiment, the following filter is used.

Figure 3:
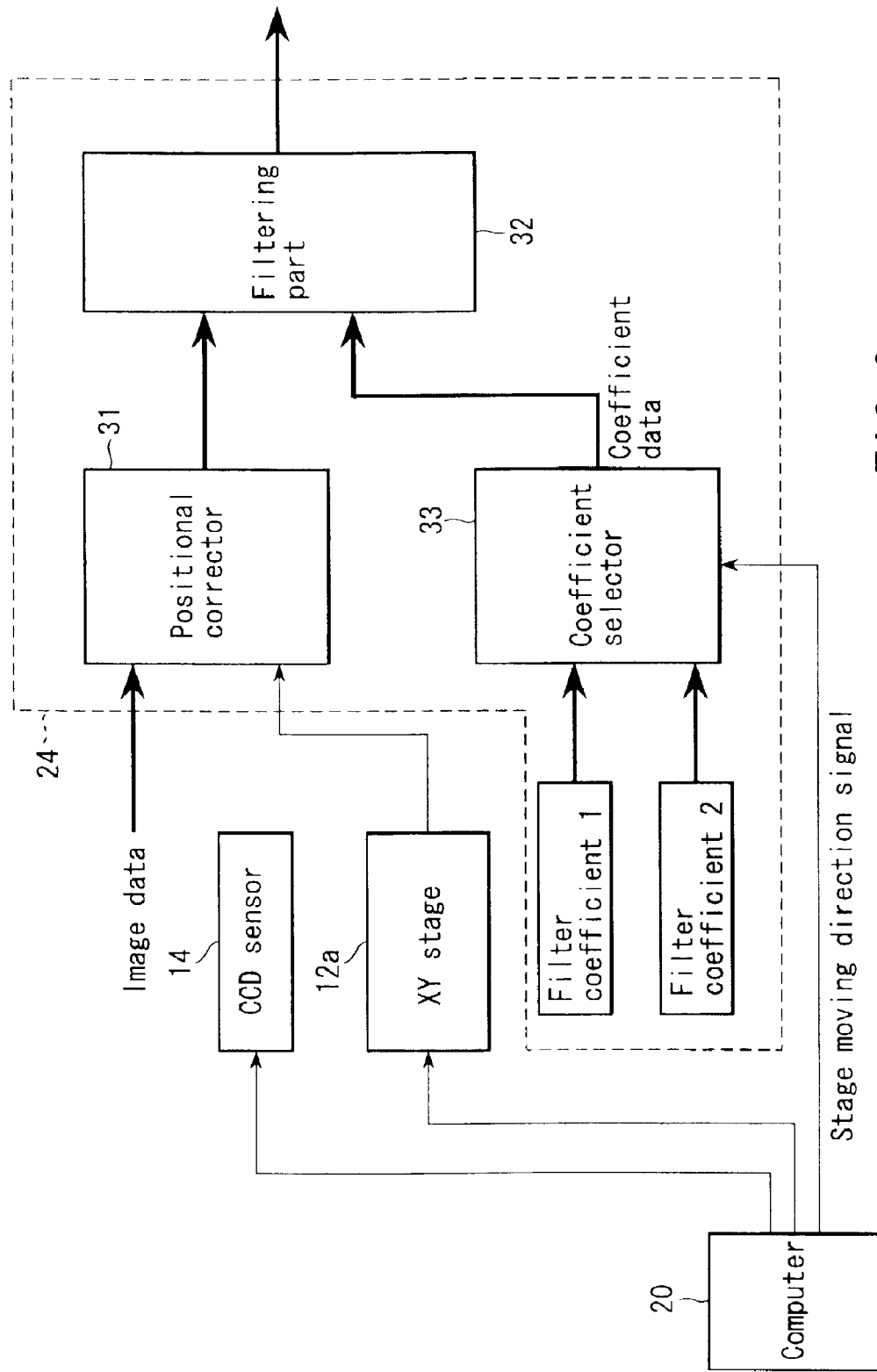
FIG. 3 is a block diagram showing the configuration of a reference part using the defect inspection apparatus of FIG. 1.

FIG. 3 is a block diagram showing the specific configuration of the reference data generator 24 which is the feature of the present embodiment. The reference data generator 24 includes a positional corrector 31 which corrects the position of normal image data, a filtering part 32 which subjects the normal image data to a filtering process to derive reference data, and a coefficient selector 33 which selects a filter coefficient used in the filtering part 32.

Reference image data is input to the positional corrector 31 together with stage position information. The positional corrector 31 outputs an image of an area corresponding to the stage coordinates. The coefficient selector 33 selects one of two sets of filter coefficients 1 and 2 according to the moving direction of the stage 12. Each set of filter coefficients contains a plurality of filter coefficients for each moving direction. The coefficient selector 33 outputs filter coefficient data for each pixel from the selected filter coefficient set to the filtering part 32.

More specifically, the filter coefficient set 1 and set 2 used in the filtering part 32 are selected according to the moving direction of the stage 12. The filtering part 32 includes a finite response filter having asymmetrical filter coefficients and performs the filtering process based on coefficient data selected by the coefficient selector 33.

Figure 4:
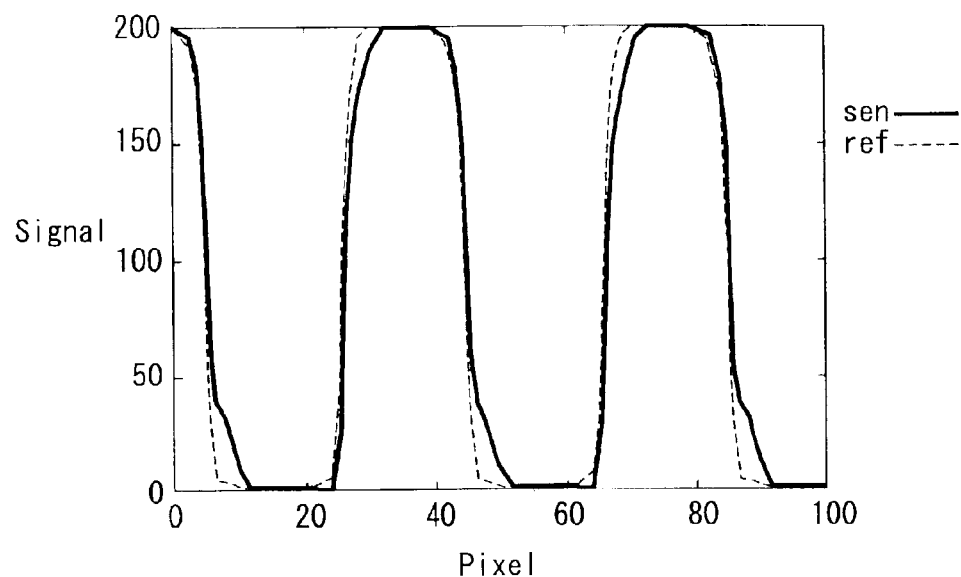
FIG. 4 is a diagram showing the result obtained by simulating an image lag effect.

FIG. 4 is a cross-sectional diagram of an image obtained by simulating an image lag effect. Reference data (ref) indicated by broken lines in FIG. 4 indicates a symmetrical image cross section, and scanned data (sen) indicated by a solid line indicates an asymmetrical image cross section. There is a risk that a false defect will occur if the difference between the above two data items cannot be neglected, and in this case, it is necessary to lower the sensing sensitivity to perform an inspection.

Figures 5A, 5B, 5C:
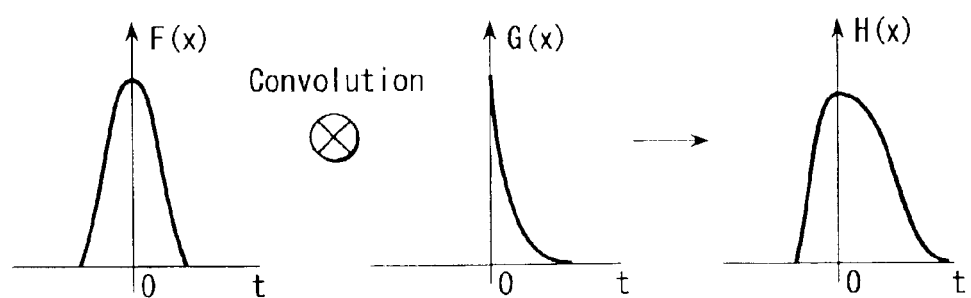
FIGS. 5A to 5C are diagrams for illustrating the operation of a filtering part in the present embodiment.

FIGS. 5A to 5C show the filtering operation in the filtering part 32. For simplicity, the case of one dimension is explained below. In order to create the reference data, the transfer function F(x) of imaging optics shown in FIG. 5A and the transfer function G(x) which expresses the image lag characteristic of the sensor shown in FIG. 5B are subjected to convolution to derive a total optical characteristic H(x) shown in FIG. 5C.

The transfer function of the imaging optics may be asymmetrical because of the influence of lens aberration or the like in some cases, but generally has a symmetrical characteristic. On the other hand, the image lag characteristic of the sensor has an asymmetrical characteristic expressed by the first-order delay function. In this case, the term "symmetrical" indicates that F(-x)=F(x) can be substantially established and the term "asymmetrical" indicates that G(-x)=G(x) cannot be substantially established.

Thus, instead of overall tuning, tuning parameters can be independently determined by separating the transfer function of the imaging optics and the characteristic of the sensor from each other and independently modeling them. As a result, the effect that tuning operation can be made simple can be attained. In this case, the effect can be attained if the transfer function for the sensor image lag is an asymmetrical function, and therefore, the function is not limited to the first-order delay function.

However, in this example, the case where a first-order delay function G(x) expressed by an equation (1) which will be described later is used is explained. T is the relaxation time and an image lag becomes larger as the value of T becomes larger. The relaxation time is set according to the practical sensor characteristic. As the sensor characteristic, (1) stage moving direction, (2) the number of integration stages, (3) integration time and the like can be considered. Items (2) and (3) are considered when a time delay and integration-type sensor such as a TDI sensor is used.

$$G(t) = \begin{cases} \frac{1}{T}\exp\left(-\frac{t}{T}\right) & \text{if } t > 0 \\ 0 & \text{otherwise} \end{cases} \quad (1)$$

The time delay and integration-type sensor is a sensor which can intensify a signal by the number of stages by transferring charges in the vertical direction in synchronism with the movement of the stage and integrating the charges with respect to an image obtained by use of a light source of ultraviolet rays or deep ultraviolet rays to which a CCD sensor is less sensitive. Unlike the CCD transfer gates 1 and 2 of FIG. 2, bi-directional CCD transfer gates in which the transfer directions in the vertical direction become opposite depending on the moving direction of the stage can be provided. Finally, as shown in FIG. 2, accumulated charges are read in the lateral direction. In some of the CCD transfer gates, parallel output is possible in order to increase inspection throughput.

Figure 6:
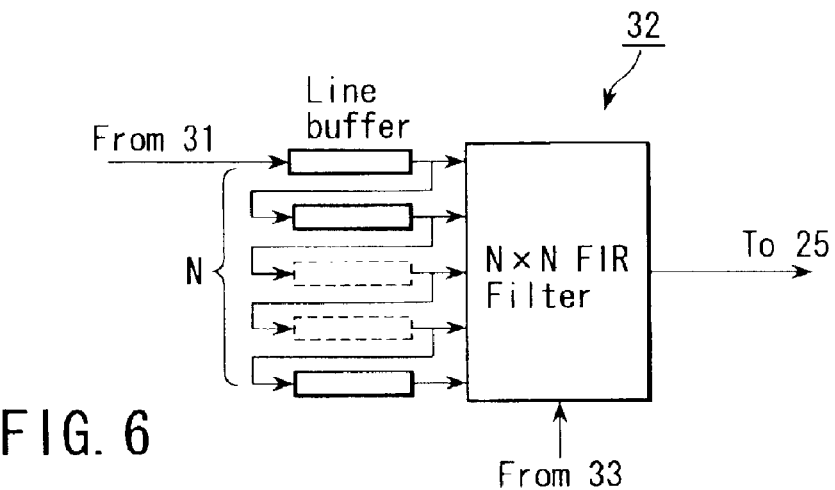
FIGS. 6 to 8 are block diagrams showing examples of a finite response filter used in the present embodiment.

In FIG. 6, one example of the finite response filter used in the present embodiment is shown. The filter generates output data to the comparator 25 by delaying input image data from the image data generator 22 by use of line-buffers of N lines and then passing the data through a finite impulse response (FIR) filter or two-dimensional finite response filter having a kernel size of N pixels×N pixels as an operation size. As filter coefficients data, data obtained by converting an overall optical characteristic H (x) which contains filter coefficient data supplied from the coefficient selector 33 into digital form is used.

Figure 7:
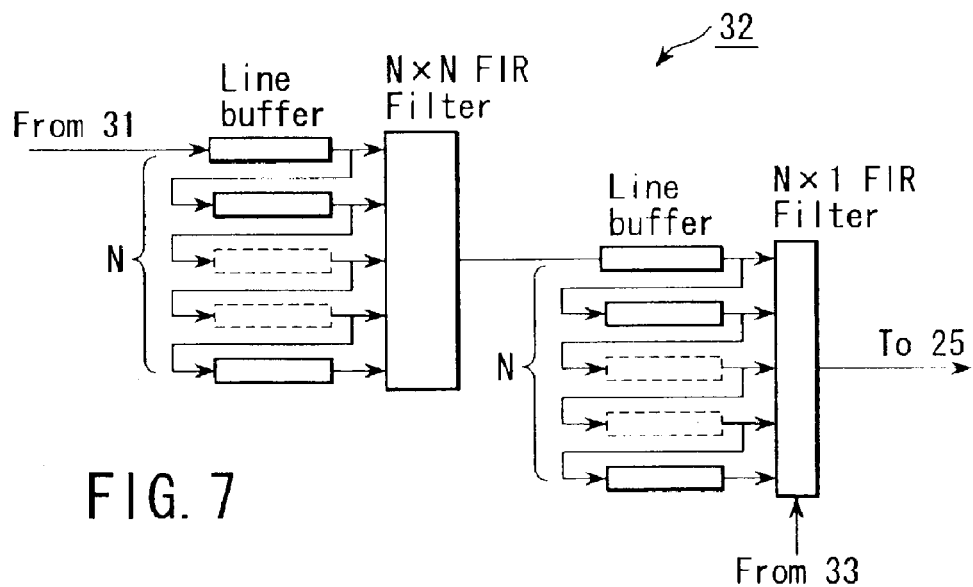

In FIG. 7, another example of the finite response filter is shown. The filter is configured by cascade-connecting a one-dimensional finite response filter to an output terminal of a preceding stage finite response filter having a kernel size of N×N. The filtering direction is set to a direction that is perpendicular to the line direction. In this case, the front FIR filter does not use the total optical characteristic H (x), but uses a function obtained by converting the transfer function F (x) into digital form. The rear FIR filter uses a function obtained by converting the transfer function G (x) into digital form. If the filters are thus separately provided for the respective transfer functions, the advantage that the filter design can be made simple can be attained.

Figure 8:
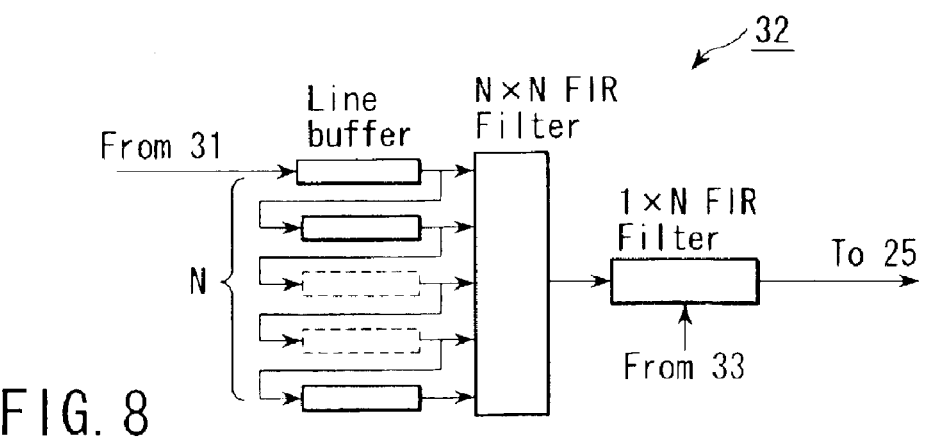

In FIG. 8, still another example of the finite response filter is shown. The filter is configured by cascade-connecting a one-dimensional finite response filter to an output terminal of the front finite response filter having a kernel size of N×N. The filtering direction is the same as the line direction. As in the case of FIG. 7, functions obtained by converting the transfer functions F (x) and G (x) into digital form are respectively set in the front FIR filter and the rear FIR filter. Even if the functions are thus set, the filter design can be made simple, as in the case of FIG. 7.

Figure 9:
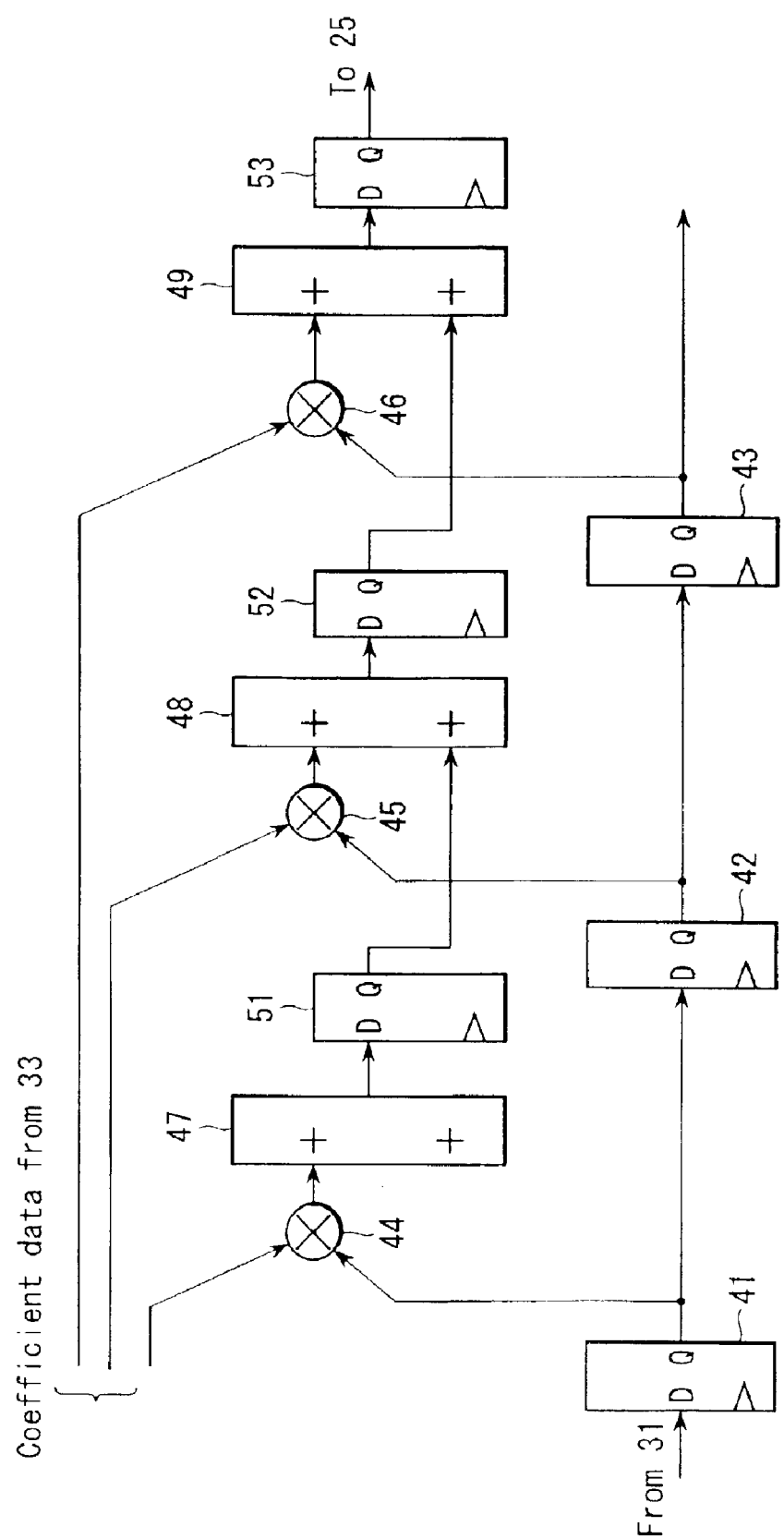
FIG. 9 is a circuit diagram showing an example of the configuration of the finite response filter.

Now, the configuration of the filtering part is explained by use of a simplified model. FIG. 9 shows an example of the FIR filter of one line×3 pixels. Input data from the positional corrector 31 is input to a first-stage D flip-flop 41 and then sequentially shifted to D flip-flops 42, 43 in synchronism with a clock.

At this time, filter coefficient data items of three pixels are supplied from the coefficient selector 33, coefficient data of the first pixel is multiplied by the output of the D flip-flop 41 in a multiplier 44, and the resultant data is supplied to and held in a D flip-flop 51 via an adder 47. The data thus held is input to a second pixel adder 48 in response to the next clock.

Likewise, data held in the second pixel D flip-flop 42 is input to a multiplier 45 together with filter coefficient data of a second pixel in synchronism with the clock, and the resultant data is added to data held in the D flip-flop 51 in the adder 48 and then held in the D flip-flop 52. The operation for a third pixel is the same as that for the second pixel.

If the above filtering process is performed, an image with an image lag as shown in FIG. 10A, for example, can be correctly formed to be reference data. In FIG. 10A, the TDI sensor is arranged on the left-hand side and charges accumulated in a line form are transferred in the right direction to sequentially form an image.

Figure 11A:
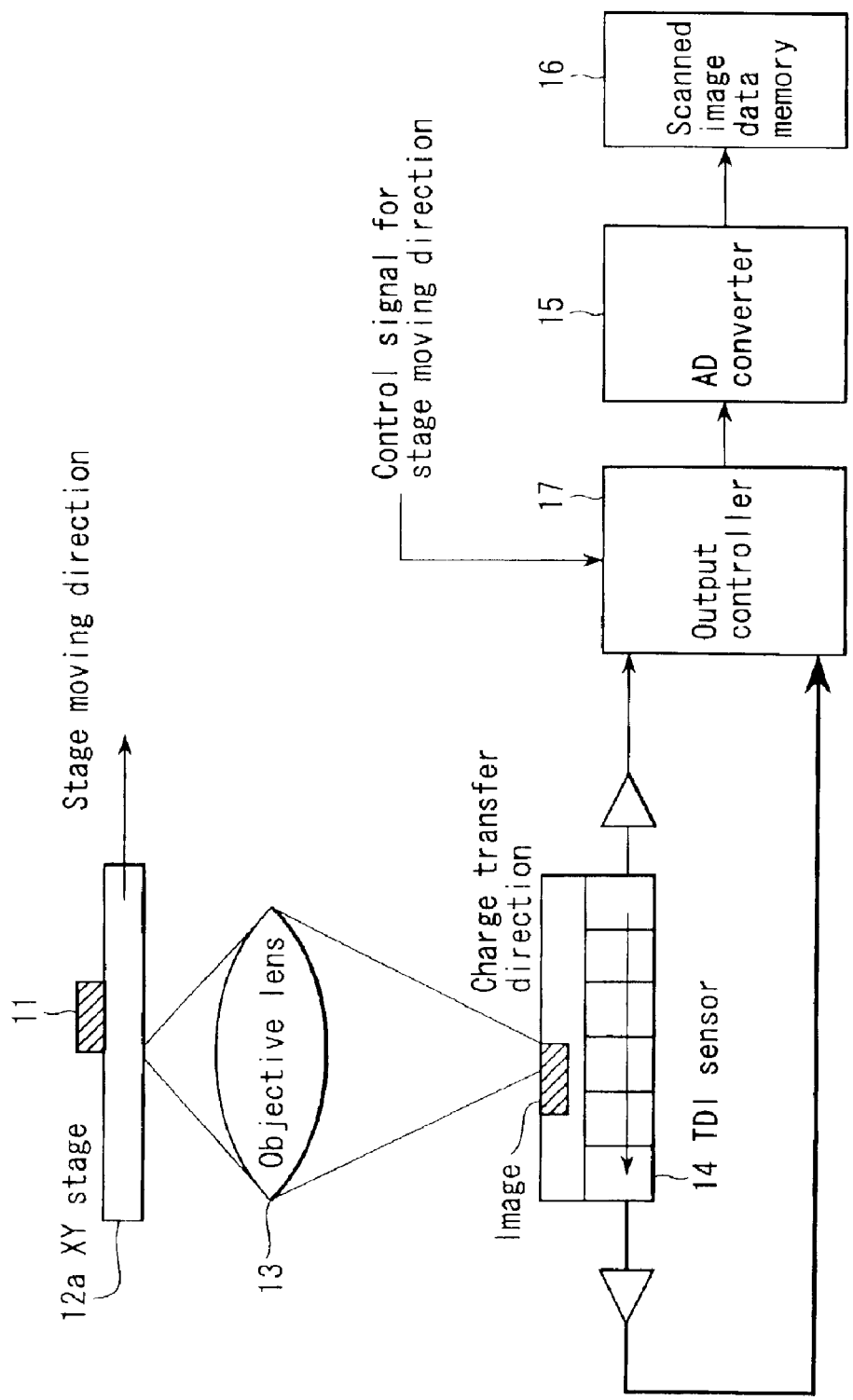
FIGS. 11A and 11B are diagrams showing the relationship between the stage moving direction and the integrated charge moving direction of the TDI sensor.
Figure 11B:
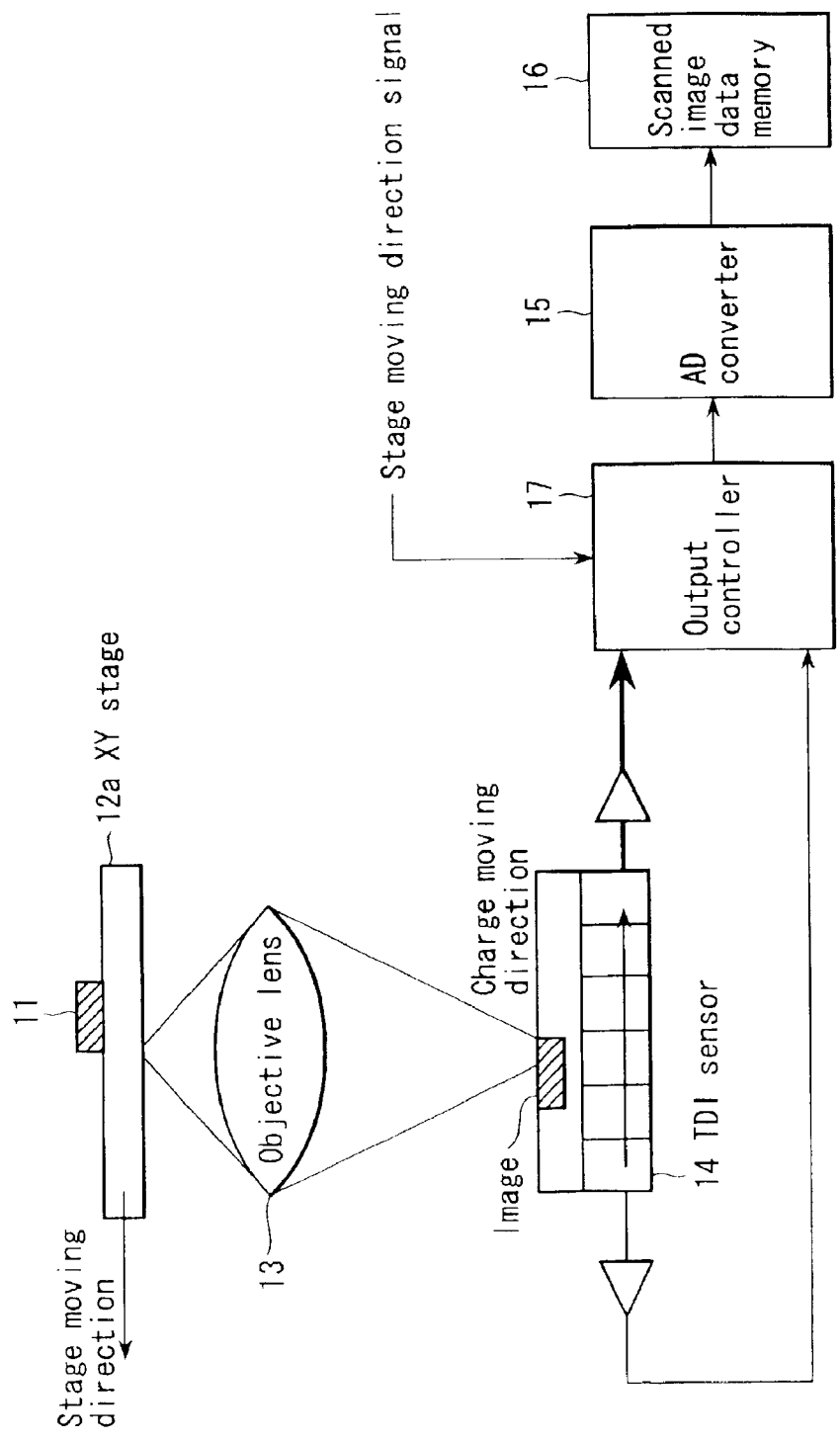

FIGS. 11A and 11B show the relationship between the moving direction of the stage 12a and the successive movement scanning direction of the TDI sensor 14. If the stage 12a which mounts the plate to be inspected 11 is caused to travel in the right direction as shown in FIG. 11A, the image moves in the left direction on the TDI sensor 14. The TDI sensor 14 transfers charges to follow the moving image. In FIG. 11B, the case where the stage 12a is moved in the left direction is shown.

Figure 12A:
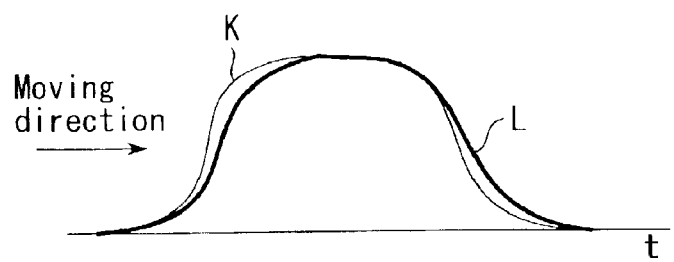
FIGS. 12A and 12B are diagrams showing the difference in the cross section of an image caused by a difference in the stage moving direction.
Figure 12B:
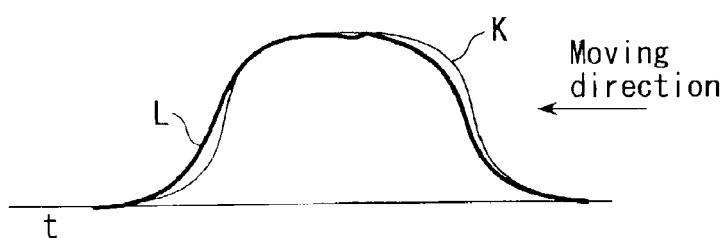

FIGS. 12A and 12B show image cross sections obtained when the TDI sensor is used and the stage 12a is continuously moved in a preset direction. In this case, K indicates the ideal image cross section and L indicates the image cross section with image lag. FIG. 12B shows the case in which the scanning direction is opposite to that of the case of FIG. 12A. Since the direction of an image lag is different depending on the scanning direction, the filter coefficient is selected according to the scanning direction by use of the computer 20. That is, the effect that the degree of fidelity between scanned image data and reference data is enhanced can be obtained by making the filter coefficient variable according to the moving direction.

Figure 13:
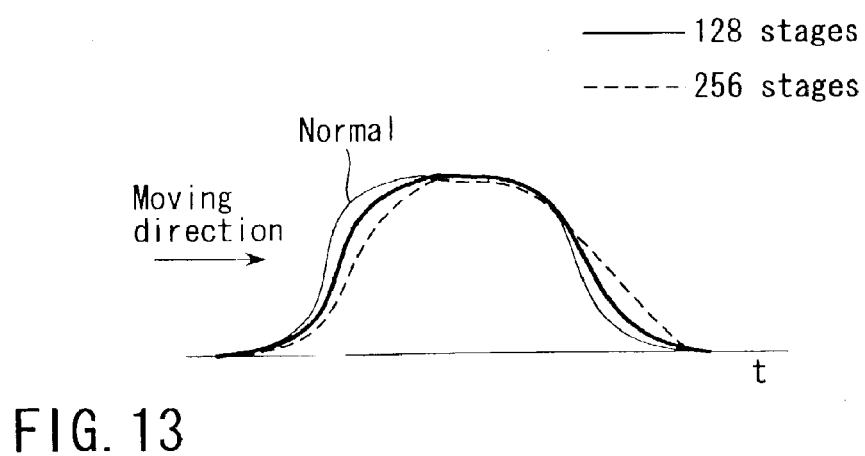
FIG. 13 is a diagram showing the variation in the cross section of the image according to the number of integration stages of the TDI sensor.

FIG. 13 shows image cross sections in the continuous moving scanning process depending on the number of integration stages of the TDI sensor. As the number of integration stages becomes larger, the effect of an image lag becomes more significant. In such a case, the effect that the degree of coincidence between a scanned image and a reference image is enhanced can be obtained by making the filter coefficients easy to vary according to the number of integration stages by use of the computer 20.

As described above, according to the present embodiment, reference data which can conform with scanned image data with a higher degree can be generated by configuring the reference data generator 24 by use of the finite response filter having the asymmetrical coefficients as shown in FIGS. 6 to 8, subjecting image data formed to express CAD data in gray level to a filtering process, and selectively switching two filter coefficient sets of the finite response filter according to the moving direction of the stage 12a. Then, occurrences of false defects can be prevented and defect inspection can be performed with high sensitivity by comparing the reference data with scanned image data by the comparator 25.

Modification

This invention is not limited to the above embodiment. In the present embodiment, a photomask is used as the plate to be inspected, but this invention is not limited to a photomask and can be applied to a printed circuit board, liquid crystal substrate or the like. The important point is that this invention can be applied to any substrate or the like on which various types of patterns having a light transmission factor or reflection factor different from that of the substrate or the like are formed.

Further, the sensor to scan an image of the plate to be inspected is not necessarily limited to the time delay and integration sensor and a conventional CCD sensor can be used. In addition, it is not limited to the CCD sensor and any type of sensor which can optically scan a pattern image on the plate to be inspected can be used. The configuration of the finite response filter implementing the reference data generator is not limited to the configurations shown in FIGS. 6 to 8 and can be adequately changed according to the specification.

In the present embodiment, the XY stage having the plate to be inspected mounted thereon is moved, but instead of this, optics and a sensor such as a CCD sensor can be moved.

As described above in detail, according to the invention, the degree of coincidence between scanned data and reference data is enhanced by using the finite response filter which switches the filter coefficients according to the relative moving direction of the plate to be inspected and the sensor, accurately modeling the characteristic of scanned data and generating reference data. As a result, occurrences of false defects are prevented and defect inspection is performed with high sensitivity and high precision.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect inspection apparatus comprising:
   a stage on which a plate to be inspected having a circuit pattern is mounted and which is movable in an X direction and in a Y direction perpendicular to the X direction;
   a sensor which optically scans the circuit pattern to obtain scanned image data;
   a scanned image data memory which stores the scanned image data in digital form;
   a normal image data generator which generates normal image data expressed by use of multiple values based on computer-aided design data relating to the circuit pattern;

a reference data generator which corrects the normal image data to generate reference data, the reference data generator including a positional corrector which corrects a position data of the normal image data, a filtering part which subjects the normal image data to a filtering process, and a filter coefficient selector which has a plurality of sets of filter coefficients, selects one of the sets of filter coefficients and extracts a desired filter coefficient data used in the filtering part from the one selected from the plurality of filter coefficient sets; and a comparator which compares the reference data with the scanned image data, wherein the filtering part comprises a first finite response filter having substantially symmetrical coefficients and a second finite response filter having a first-order lag function, the first and second finite response filters having respective transfer functions which are subjected to convolution.

2. The defect inspection apparatus according to claim 1, wherein the filtering part includes a finite response filter having asymmetrical coefficients.

3. The defect inspection apparatus according to claim 1, wherein the first-order lag function is variable only in one of the X and Y directions.

4. The defect inspection apparatus according to claim 1, wherein the filter coefficient selector selects the desired filter coefficient data according to whether a moving direction of the stage is the X direction or the Y direction.

5. The defect inspection apparatus according to claim 1, wherein the sensor is a time delay and integration sensor which moves integrated charges in a direction opposite to a moving direction of the stage.

6. The defect inspection apparatus according to claim 1, wherein the sensor is a time delay and integration sensor which alternatively scans the plate to be inspected and the filter coefficient selector selects the desired filter coefficient data according to a scanning direction of the sensor.

7. The defect inspection apparatus according to claim 1, wherein the sensor is a time delay and integration sensor and the filter coefficient selector selects the desired filter coefficient data according to the number of integration stages of the time delay and integration sensor.

8. The defect inspection apparatus according to claim 1, wherein the sensor is a time delay and integration sensor and which further comprises an output controller which controls output of the scanned image data according to a scanning direction of the sensor.

9. The defect inspection apparatus according to claim 8, further comprising an analog-to-digital converter which digitizes an output of the output controller and supplies a result of digitization to the scanned image data memory.

10. The defect inspection apparatus according to claim 1, further comprising a control computer which controls operations of the normal image data generator, the stage, the reference data generator and the sensor.

11. A defect inspection apparatus comprising:

a sensor which optically senses a circuit pattern formed on a plate to be inspected to obtain scanned image data of the circuit pattern while moving relatively to the plate to be inspected;

an analog-to-digital converter which converts the scanned image data into digital form;

a normal image data generator which derives normal image data expressed by use of multiple values based on computer-aided design data relating to the circuit pattern;

a reference data generator which processes the normal image data to generate reference data while selecting filter coefficients according to a moving direction of the plate to be inspected by use of a finite response filter having asymmetrical coefficients; and a comparator which compares the reference data with the scanned image data, wherein the finite response filter includes a first finite response filter having substantially symmetrical coefficients and a second finite response filter having a first-order lag function, the first and second finite response filters having respective transfer functions which are subjected to convolution.

12. The defect inspection apparatus according to claim 11, further comprising an XY stage having the plate to be inspected mounted thereon and being movable in X and Y directions, wherein the first-order lag function is variable only in one of the X and Y directions.

13. The defect inspection apparatus according to claim 11, wherein the filter coefficient data of the second finite response filter is selected according to a moving direction of the XY stage.

14. The defect inspection apparatus according to claim 11, wherein the sensor is a time delay and integration sensor which periodically scans the plate to be inspected and the filter coefficient data of the second finite response filter is selected according to a scanning direction of the sensor.

15. The defect inspection apparatus according to claim 11, wherein the sensor is a time delay and integration sensor and the filter coefficient data of the second finite response filter is selected according to a number of integration stages of the sensor.

16. The defect inspection apparatus according to claim 11, wherein the comparator determines that there is no defect if a difference between the scanned image data and the reference data is within a permissible limit and determines a presence of a defect if the difference between the scanned image data and the reference data exceeds the permissible limit.

* * * * *